United States Patent
Bookwalter et al.

(10) Patent No.: US 6,808,493 B1
(45) Date of Patent: Oct. 26, 2004

(54) ADJUSTABLE RATCHET RETRACTOR SUPPORT APPARATUS

(76) Inventors: John R. Bookwalter, 20 Roberts Farm La., Putney, VT (US) 05346; Jonathan Adler, 507 Sterling La., Upper Brookville, NY (US) 11771; Bernd D. Ascher, 75 Richard Ave., Islip Ter., NY (US) 11752; Leonard Coraci, Jr., 15 Ocala Ct., Selden, NY (US) 11784

( * ) Notice: Subject to any disclaimer, the term of this patent is extended or adjusted under 35 U.S.C. 154(b) by 154 days.

(21) Appl. No.: 10/229,435

(22) Filed: Aug. 28, 2002

(51) Int. Cl.[7] .................................................. A61B 1/32
(52) U.S. Cl. ....................................... 600/233; 600/231
(58) Field of Search ................................. 600/228, 229, 600/230, 234, 215, 222, 233, 231

(56) References Cited

U.S. PATENT DOCUMENTS

| | | |
|---|---|---|
| 1,919,120 A | 7/1933 | O'Connor et al. |
| 1,963,173 A | 6/1934 | Morin |
| 4,254,763 A | 3/1981 | McCready et al. |
| 4,421,108 A | 12/1983 | Cabrera et al. |
| 4,424,724 A | 1/1984 | Bookwalter et al. |
| 4,434,791 A | 3/1984 | Darnell |
| 4,467,791 A | 8/1984 | Cabrera et al. |
| 4,949,707 A | 8/1990 | LeVahn et al. |
| 5,320,444 A | 6/1994 | Bookwalter et al. |
| 5,356,100 A | 10/1994 | Bookwalter et al. |
| 5,365,921 A | 11/1994 | Bookwalter et al. |
| 5,375,481 A | 12/1994 | Cabrera et al. |
| 5,520,608 A | 5/1996 | Cabrera et al. |
| 5,520,610 A | 5/1996 | Giglio et al. |
| 5,529,358 A | 6/1996 | Dinkler et al. |
| 5,795,291 A | 8/1998 | Koros et al. |
| 6,241,659 B1 | 6/2001 | Bookwalter et al. |
| 6,322,500 B1 * | 11/2001 | Sikora et al. ............... 600/219 |

* cited by examiner

*Primary Examiner*—Cary E. O'Connor
*Assistant Examiner*—Candice C. Melson (57) ABSTRACT

An adjustable ratchet retractor support apparatus includes in one aspect a rotatable locking mount having first and second surfaces and an axis of rotation perpendicular to the surfaces. First and second rotatable pivot members are disposed respectively on the first and second surfaces for rotation around the axis of rotation. Each of the pivot members include ratchet teeth. First and second curved arm members are mounted respectively on and associated respectively with the first and second pivot members. Each of the arm members is rotatable about a respective axis of rotation perpendicular to the axis of rotation of the locking mount. Each arm member has mounted thereon a ratchet pawl for engagement with the ratchet teeth of the associated pivot member. First and second rotatable clamps are disposed respectively on the first and second pivot members for restraining rotation of the pivot members.

10 Claims, 9 Drawing Sheets

ADJUSTABLE RATCHET RETRACTOR SUPPORT APPARATUS

BACKGROUND OF THE INVENTION

1. Field of the Invention

The present invention relates to an adjustable ratchet retractor support apparatus useful, for example, in abdominal, thoracic and orthopedic surgery.

2. The Prior Art

In many surgical operations it is customary to employ a table-fixed retraction apparatus in which a frame or mounting ring rests over the patient surrounding the surgical opening, and a number of retractors may be movably attached to the frame and flexibly positioned, with various clamping or positioning mechanisms, to reach into the surgical opening and retract surrounding or obstructing tissue or organs, or to stabilize or position tissue or organs that are being worked on. In general, such retractors may include a blade or spoon-like member, or various gripping members, that each extend from an elongated handle or stem, and the stem moves within a clamping mechanism that mounts on the mounting ring and locks the blade or gripping member in a selected position. The clamping mechanism may itself have a mechanical structure allowing one or more additional degrees of movement in rotation or displacement, so that both the position and orientation of the blade may be quickly set and locked. Various common machine elements such as swivel ball mounts, arcuate rack or tilt mounts, ratchet or rack adjustment and locking mechanisms, or screw clamps may be incorporated in the clamping structures to provide assemblies that are moved by hand into the desired position and locked.

By way of example, one commercially useful system is shown in the various patents of John R. Bookwalter et al., such as U.S. Pat. Nos. 4,424,724; 4,254,763; 4,421,108; 5,375,481; and 5,520,608. This system is made and marketed by Codman. In the Bookwalter system, the frame element is a is a flat ring with regular notches. The ring is held by a post that clamps to the side rail of the operating table, so the ring is suspended in a plane above the surgical site. The plane of the ring sets one constraint on the movement of the retractor units, and allows the various retractor clamp assemblies to move into position and lock with a sliding movement that is conveniently set with one hand. This system is discussed in Bookwalter et al. U.S. Pat. No. 6,241,659.

Other surgical retractor systems are shown in LeVahn et al. U.S. Pat. No. 4,949,707; O'Connor et al. U.S. Pat. No. 1,919,120; Giglio et al. U.S. Pat. No. 5,520,610; Morin U.S. Pat. No. 1,963,173; Darnell U.S. Pat. No. 4,434,791; Dinkler et al. U.S. Pat. No. 5,529,358; and Koros et al. U.S. Pat. No. 5,795,291.

Although a number of retractor systems are known, there is still a need for a retractor support apparatus with the ability to open or close either side of a two-piece ring independently using a quick-release ratchet mechanism that allows rapid positioning of the ring to provide increased exposure to the operative incision without having to make other adjustments.

SUMMARY OF THE INVENTION

An adjustable ratchet retractor support apparatus is provided. In one aspect, the apparatus includes a rotatable locking mount, first and second rotatable pivot members, first and second curved arm members, and first and second rotatable clamps.

The locking mount has first and second surfaces and an axis of rotation perpendicular to these surfaces.

The pivot members are disposed respectively on the first and second surfaces of the locking mount for rotation around the axis of rotation. Each of the pivot members include ratchet teeth.

The arm members are mounted respectively on and associated respectively with the first and second pivot members. Each of the arm members is rotatable about a respective axis of rotation perpendicular to the axis of rotation of the locking mount. A ratchet pawl is mounted on each arm member for engagement with the ratchet teeth of the associated pivot member.

The clamps are disposed respectively on the first and second pivot members for restraining rotation of the pivot members.

In another aspect, the apparatus includes a connector including first and second sets of ratchet teeth and first and second curved arm members mounted to the connector. Each of the arm members is rotatable around a respective axis of rotation perpendicular to the connector. Each arm member also has mounted thereon a respective ratchet pawl for engagement with a corresponding one of the sets of ratchet teeth.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawing, wherein similar reference characters denote similar elements throughout the several views.

DETAILED DESCRIPTION OF PREFERRED EMBODIMENTS

Figure 1A:
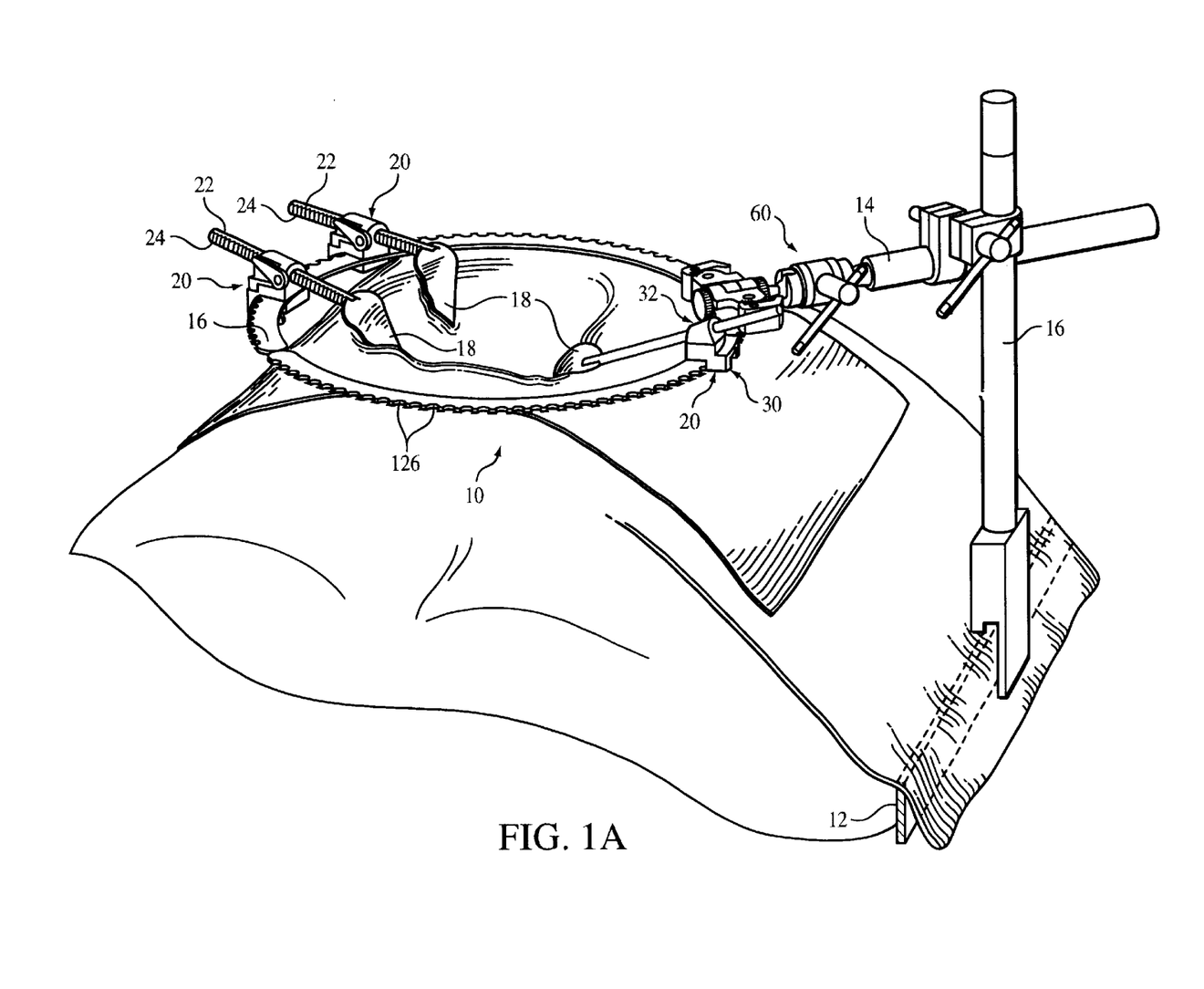
FIG. 1A shows a perspective view of a first embodiment of the adjustable ratchet retractor support apparatus mounted on a vertical support with retractor blades mounted thereon.
Figure 1B:
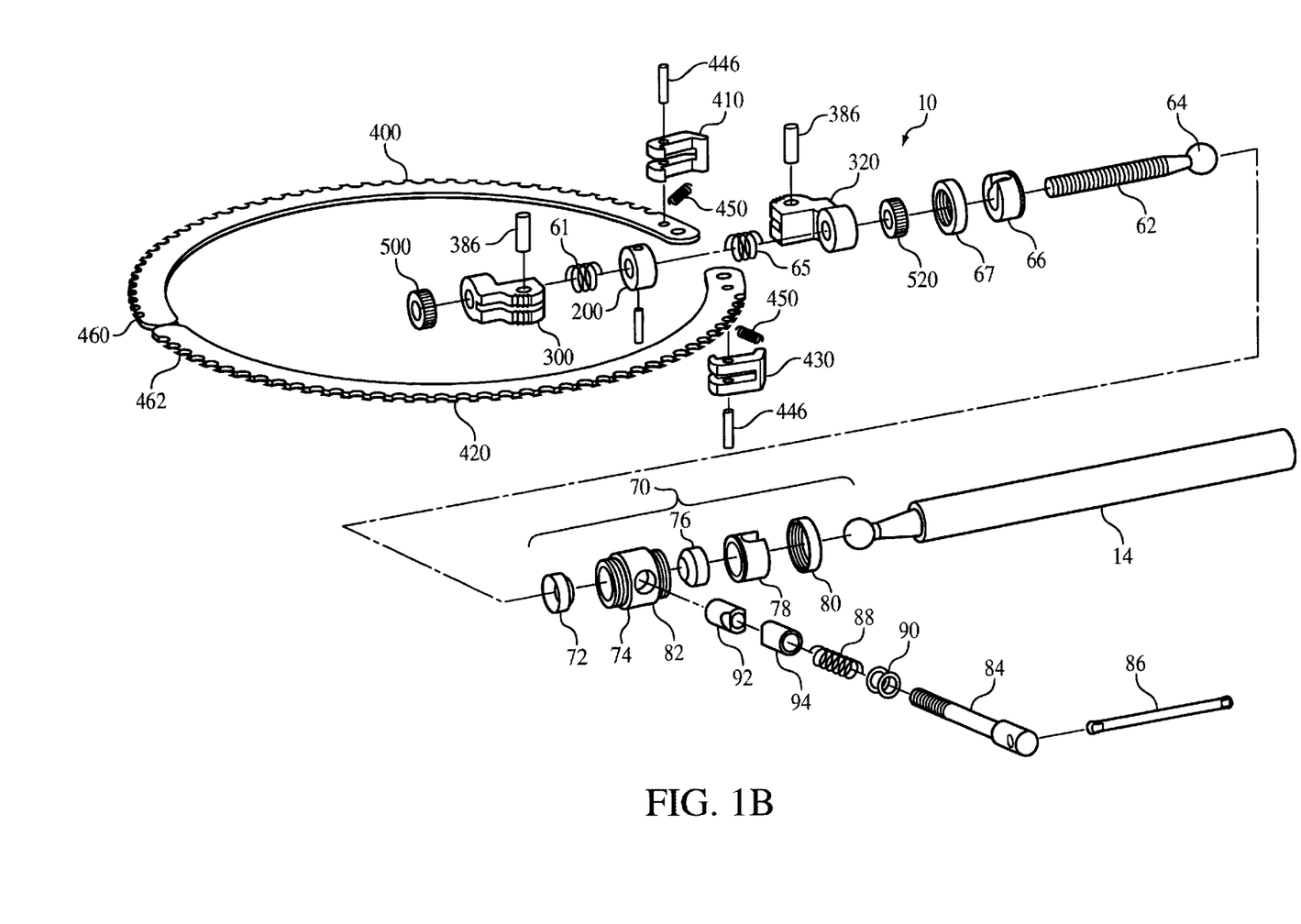
FIG. 1B shows an exploded view of the embodiment, and ball post assembly and arm shown in FIG. 1A.
Figure 2:
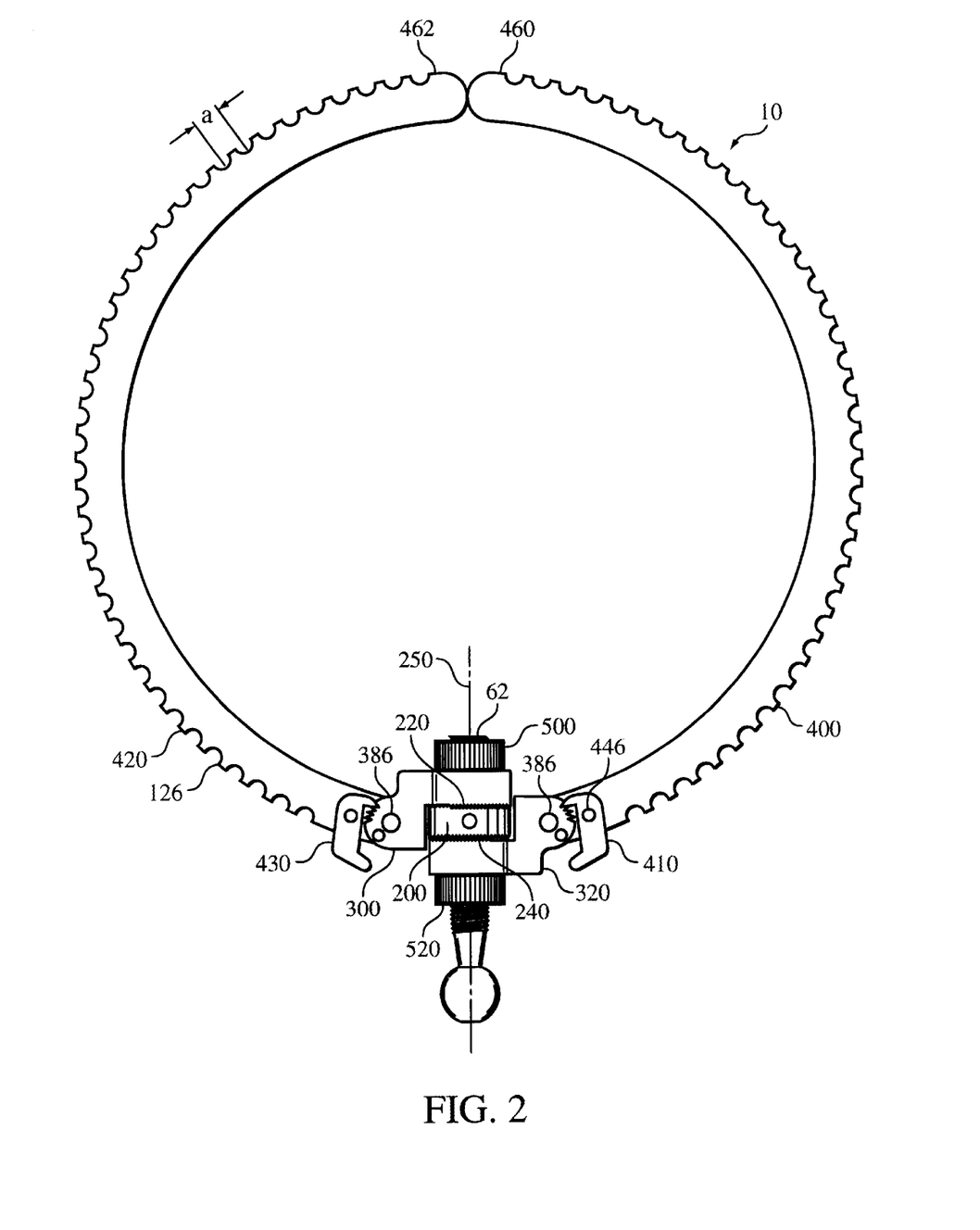
FIG. 2 is an elevation view of the embodiment of FIG. 1A.

Turning now in detail to the drawings, FIGS. 1A, 1B and 2 show an adjustable ratchet retractor support apparatus of a preferred embodiment. Apparatus 10 is supported by a ball post assembly 60 which in turn is supported by an arm 14 extending over the patient. Arm 14 may be connected to a vertical support post 16 which is clamped to the side rail 12 of an operating table on which the patient is supported.

As shown in FIG. 1B, ball 64 is received in an existing float and lock ball system 70 attached to stabilizing post 16 shown in FIG. 1A. Float and lock ball system 70 includes collar 72, coupler 74, seat 76, retainer 78, and ring 80. Coupler 74 includes opening 82 into which tightening screw 84 having wrench handle 86 is inserted. Spring 88 and O-rings 90 may be disposed around screw 84. Tightening handle 86 causes abutment pieces 92, 94 to lock ball 64 in place.

Apparatus 10 includes a rotatable locking mount 200, first and second pivot members 300, 320, first and second curved arm members 400, 420 and first and second rotatable clamps or thumb screws 500, 520 disposed on the shaft 62 of ball post assembly 60. A number of retractor blades 18 carried by respective ratchet locking mechanisms 20 may be supported by curved arm members 400, 420. Each retractor blade 18 includes a long shaft or stem 22 along one side of which is included a rack or ratchet track 24. Retractor blades 18 extend into the surgical opening for retracting tissue. The clamping or ratchet mechanisms 20, are configured to fix the position on arm members 400, 420 as well as to set the extension or angle of the retractor blades 18, with one or more simple clamping motions. In the prior art such clamping or ratchet mechanisms have included ones with a square passage for accommodating a shaft of a retractor blade in a fixed orientation about its shaft, and ones with a round passageway for accommodating notched or threaded cylindrical shafts that permit the retractor blade to be rotated in an arbitrary position. The detailed construction of several suitable ratchet mechanisms is set forth in U.S. Pat. No. 5,375,481 and in U.S. Pat. No. 4,424,724. These mechanisms allow the surgeon to retract and lift an organ at the same time as they duplicate the natural toe-in or angular retraction one achieves by hand.

The present invention seeks to provide an adjustable ratchet retractor support apparatus, preferably adapted for use with known ratchet blade assemblies, which includes arm members that are easily and conveniently spread open and have quick release ratcheting mechanisms which allow rapid re-positioning of the arm members. An independent ratchet mechanism allows the ring formed by the arm members to open and be positioned independently. The arm members may be pivoted and held open in numerous positions and be positioned at a transverse angle to one another.

As shown more fully in FIG. 2, in accordance with one aspect of the present invention, rotatable locking mount 200 of apparatus 10 has first and second surfaces 220 and 240 on which first and second rotatable pivot members 300, 320 are respectively disposed. Shaft 62 of ball post assembly 60 is preferably threaded, and locking mount 200 is mounted for rotation on threaded shaft 62 about an axis of rotation 250 perpendicular to surfaces 220, 240 and running through clamps 500, 520, pivot members 300, 320 and locking mount 200.

First pivot member 300 is disposed on surface 220 and second pivot member 320 is disposed on surface 240 of locking mount 200. Each pivot member is rotatable around axis of rotation 250. Surface 220, 240 of locking mount 200 are each preferably provided with locking teeth forming a starburst or notched configuration, at least around a portion of its perimeter which mates with locking teeth forming a similar configuration provided on the respective portion of pivot members 300, 320 which interfaces with the respective surface. Rotating clamps 500, 520 around shaft 62 in one direction, preferably clockwise, causes the clamps to move along threaded shaft 62 toward pivot members 300, 320, causing pivot members 300, 320 to interface with surfaces 220, 240 of locking mount 200 and prevent pivot members 300, 320 from rotating about axis of rotation 250. Preferably, helical springs 61, 65 shown in FIG. 1B are disposed on threaded shaft 62 between locking mount 200 and pivot members 300, 320.

Figure 3A:
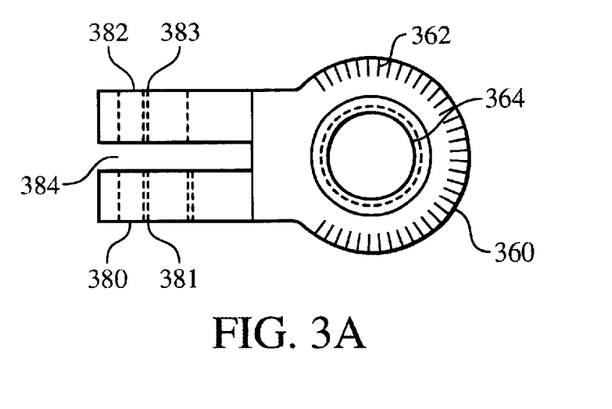
FIGS. 3A and 3B are elevational and side views respectively of a pivot member used in the embodiment of FIG. 1A.
Figure 3B:
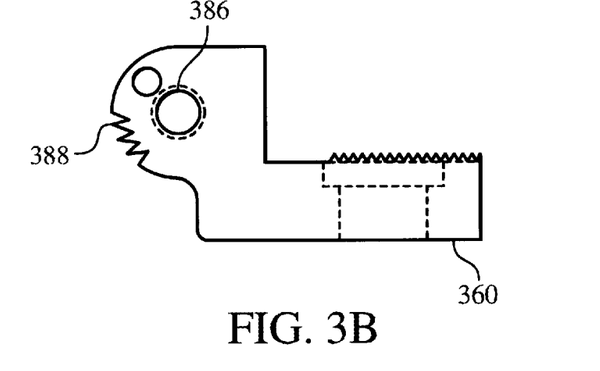

As shown in FIGS. 3A and 3B, each pivot member includes a relatively flat circular portion 360 and a pair of mounting supports 380, 382. Circular portion 360 has locking teeth 362 formed around its periphery for interfacing with the locking teeth of locking mount 200 and restraining rotation of the pivot member. Circular portion 360 also has an annular bore 364 through which threaded shaft 62 of ball post assembly extends.

Mounting supports 380, 382 form an opening or slot 384 which receives arm members 400 or 420. Arm member 400 is received within pivot member 320, and arm member 420 is received within pivot member 300. Each arm member is preferably mounted within slot 384 by a pivot screw 386 held between mounting supports 380, 382. Pivot screw 386 forms an axis of rotation for its associated arm member perpendicular to axis of rotation 250 of locking mount 200.

Each mounting support 380, 382 has an opening 381, 383 through which pivot screw 386 extends. Preferably, one opening, for example opening 381, is threaded and the other opening 383 is unthreaded so that pivot screw 386 may be tightened causing a clamping action of the mounting supports 380 and 382 to the associated arm member 400, 420. This clamping action stops the associated arm member 400, 420 from rotating freely to hold the associated arm member in place at a selected rotational position.

As shown in FIG. 3B, a portion of each mounting support 380, 382 is provided with ratchet teeth 388 for mating with a ratchet pawl 410 or 430 provided on arm member 400, 420.

Figure 3C:
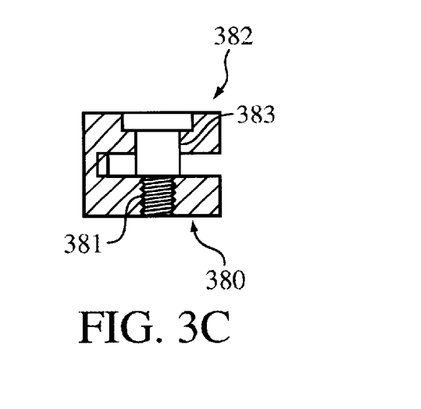
FIG. 3C is a sectional view of mounting supports of the pivot member of FIG. 3A showing a shoulder screw mounted therein.
Figure 3D:
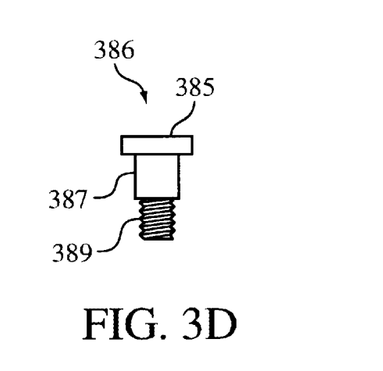
FIG. 3D is a side view of the shoulder screw shown in FIG. 3C.

As shown in FIGS. 3C and 3D, pivot screw 386 preferably is a modified precision shoulder screw having a socket head 385, an unthreaded shaft portion 387 and a threaded shaft portion 389 of reduced diameter. Alternatively, a pivot pin of uniform diameter without threads may be used in place of the pivot screw without threads being provided on the opening of the mounting support.

Figure 4A:
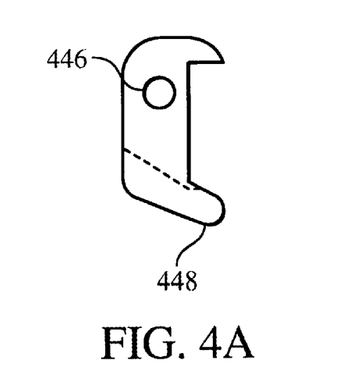
FIGS. 4A and 4B are side and elevational views respectively of a ratchet pawl used in the embodiment of FIG. 1A.
Figure 4B:
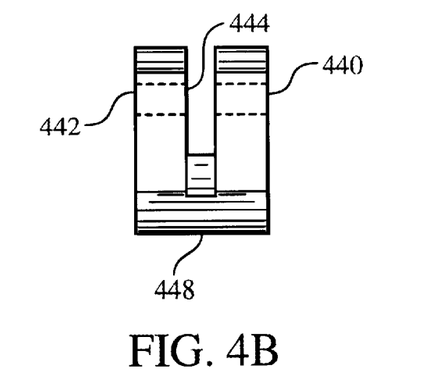
Figure 5:
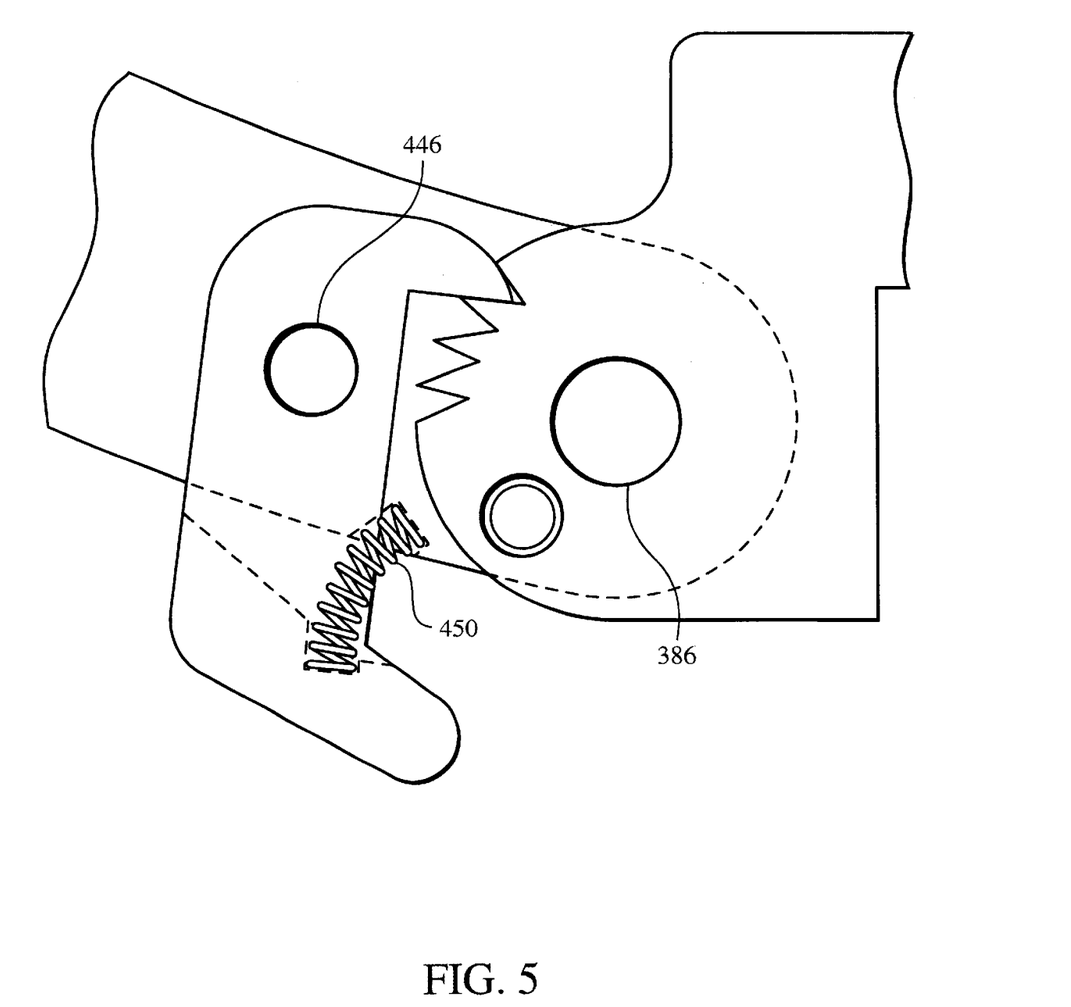
FIG. 5 is an enlarged view of the ratchet pawl of FIGS. 4A and 4B shown engaging the ratchet teeth of the pivot member of FIGS. 3A and 3B.

As shown in FIGS. 4A and 4B, each ratchet pawl includes a lever handle section 448 and ratchet pawl members 440, 442. Ratchet pawl members 440, 442 form an opening or slot 444 through which arm member 400 or 420 extends. A pivot pin 446 disposed between ratchet pawl members 440, 442 mounts each ratchet pawl to its associated arm member for pivotal movement of the ratchet pawl members about pivot pin 446. A spring 450 disposed between lever handle section 448 and arm member 400 or 420 biases ratchet pawl members 440, 442 into engagement with ratchet teeth 388 of pivot member 300 or 320. Depressing lever handle section 448 pivots ratchet pawl members 440, 442 about pivot pin 446 to release the pawl members from engagement with the teeth.

Ratchet teeth 388 and ratchet pawl members 440, 442 restrain rotation of arm member about pivot pin 446 in one direction, preferably in the "closing" direction, i.e. the direction toward formation of a closed ring by the arms. Rotation in the opposite or "opening" direction however is allowed by the ratchet teeth and pawl members. Thus, the arms are able to be rapidly opened simply by movement of the arms and closed by depressing of the lever handle section to free the ratchet pawl members from the teeth.

Each arm member 400, 420 may be provided with a plurality of notches or indentations 126 on the outer edge of the arm to fix the circumferential position of the ratchet holder 30 of a retractor blade assembly. Preferably, the notch spacing a is between 0.4 and 0.6 inches, for example 0.375 inches.

Figure 6A:
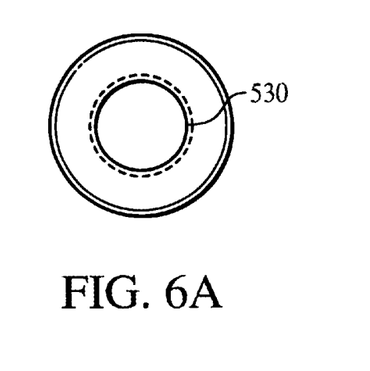
FIGS. 6A and 6B are bottom and side views, respectively, of a rotatable clamp used in the embodiment of FIG. 1A.
Figure 6B:
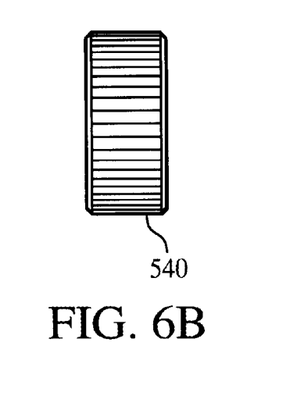

As shown in FIGS. 6A and 6B, each rotatable clamp 500, 520 has a threaded annular bore 530 for receipt of threaded shaft 62 of ball post assembly 60. Preferably, each clamp has knurling 540 to assist a user's fingers in rotating the clamp.

Figure 7:
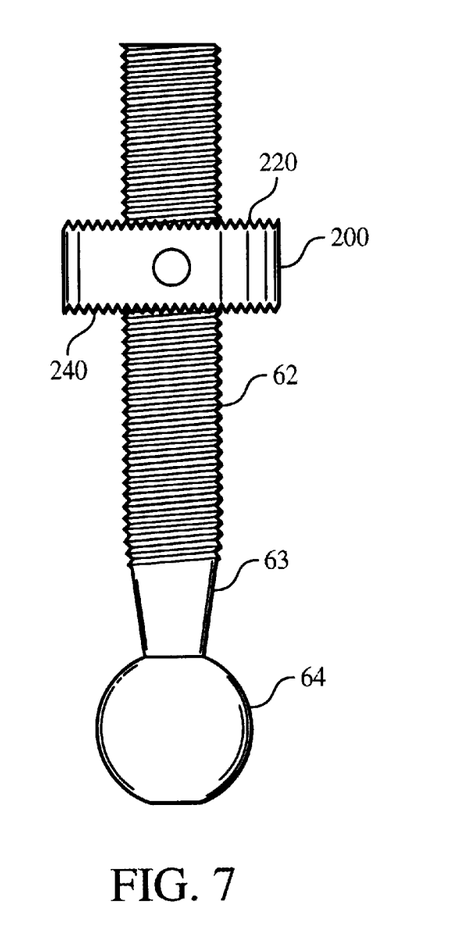
FIG. 7 is an elevational view of a locking mount used in the embodiment of FIG. 1A shown mounted on a ball post.
Figure 8A:
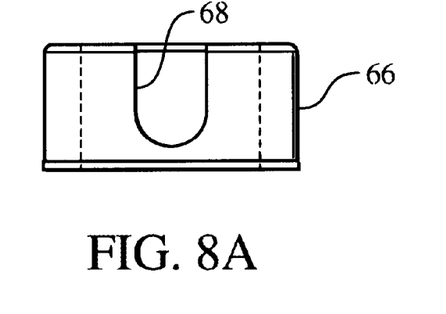
FIGS. 8A-8C are side, front and rear views, respectively, of a ball post retainer for the ball post shown in FIG. 7.
Figure 8B:
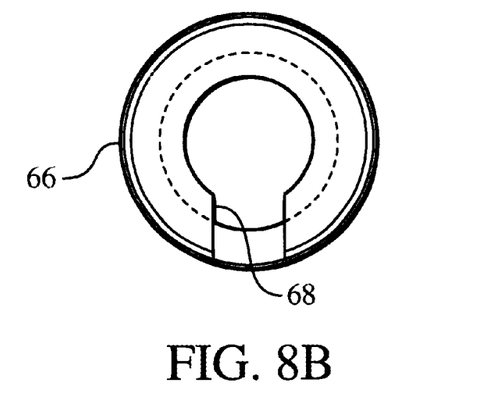
Figure 8C:
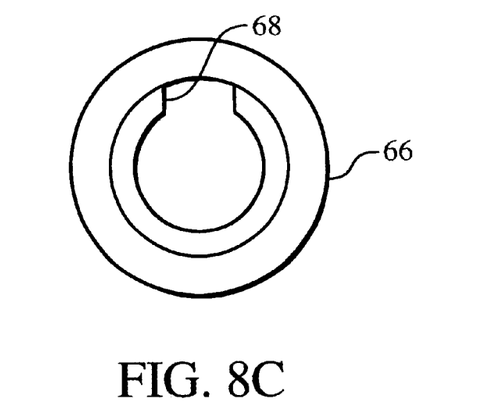

Ball post assembly includes shaft 62, connecting post 63 and ball 64 shown in FIG. 7, ball post collar 67 shown in FIG. 1B, and ball post retainer 66 shown in FIG. 8 which receives ball 64. Ball post retainer 66 has a slot 68 which restrains lateral movement of ball post 63 when received therein. Lifting ball post 63 out of slot 68 allows for movement of ball post assembly.

Preferably arm members 400, 420 form a ring in the closed position shown in FIG. 2 where the respective ends 460, 462 touch each other. Each arm member preferably is able to rotate approximately 105° about its associated pivot member so that the ends may be separated by a selected distance, for example, 11 inches. A bridge bar (not shown) may be attached at the open end to provide further support and to prevent hysteresis effect encountered in prior art round bar "wishbone" open designs, such as is shown in U.S. Pat. No. 4,949,707.

Figure 9:
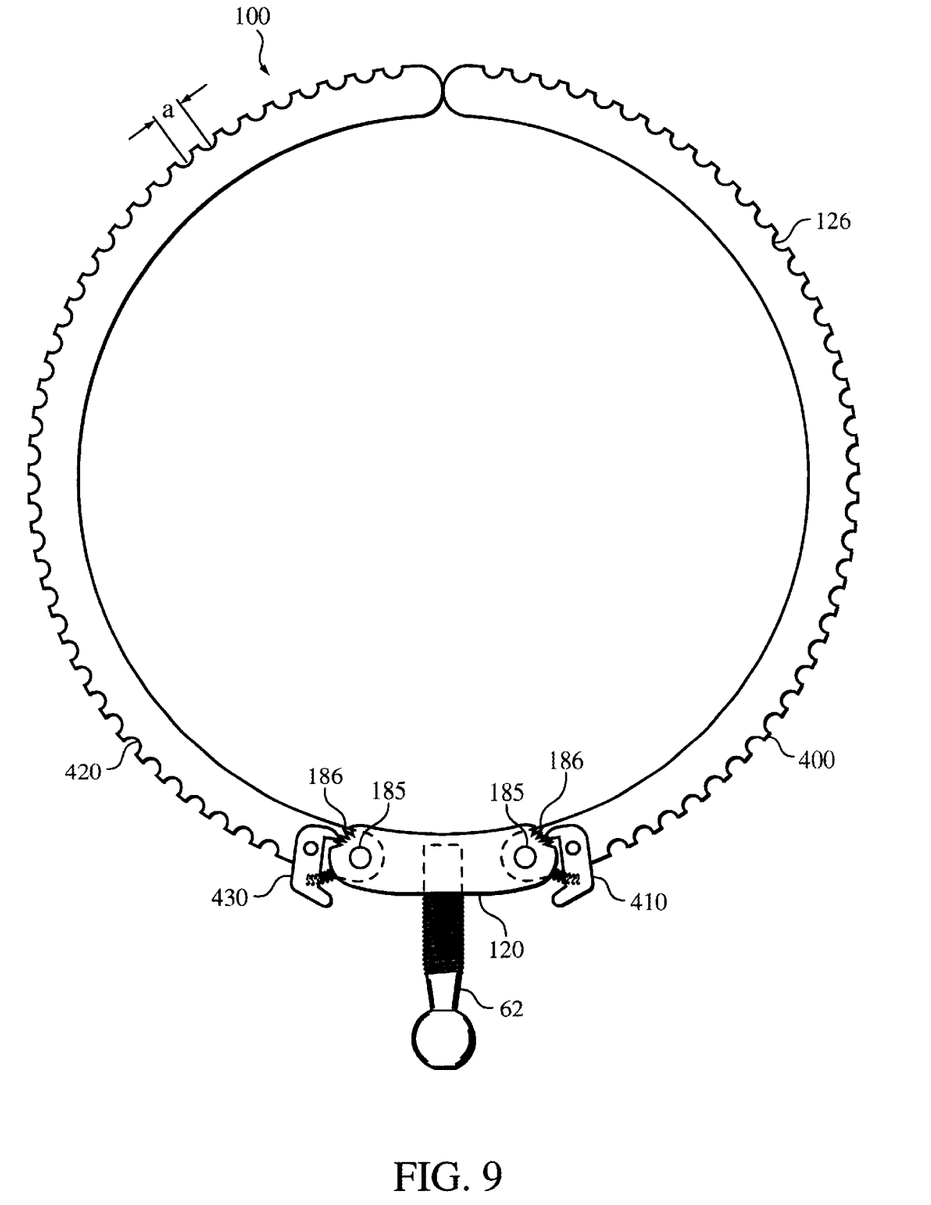
FIG. 9 is an elevation view of a second embodiment of the invention.
Figure 10A:
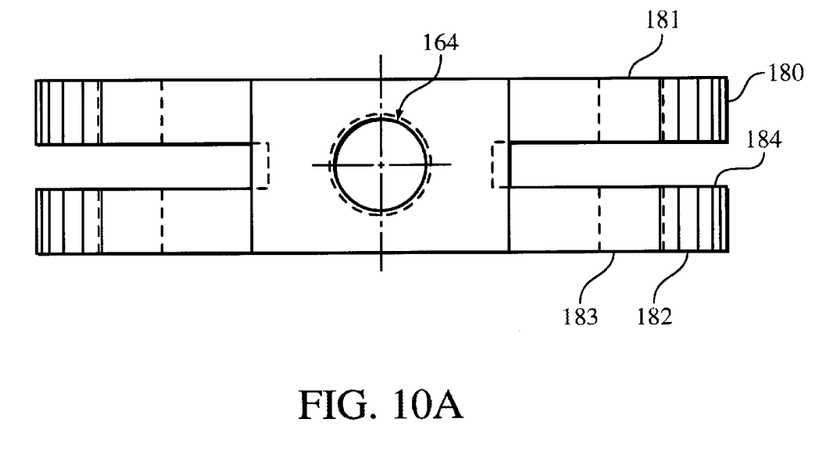
FIGS. 10A and 10B are side and elevational views, respectively, of the connector used in the embodiment of FIG. 9.

FIG. 9 shows a second embodiment of the adjustable ratchet retractor support device. The apparatus 100 includes a connector 120 including first and second sets of ratchet teeth 186, and first and second curved arm members 400, 420 mounted to connector 120. As shown in FIG. 10A, each end of connector 120 includes a pair of mounting supports 180, 182. Between the ends is a section with an annular bore 164 through which threaded shaft 62 of ball post assembly 60 extends. Mounting supports 180, 182 form an opening or slot 184 which receives arm member 400 or 420.

Each arm member is preferably mounted within its respective slot 184 by a pivot screw 185 held between mounting supports 180, 182. Pivot screw 185 forms an axis of rotation for its associated arm member perpendicular to connector 120 and the plane of arm members 400, 420. Each mounting support 180, 182 has an opening 181, 183 through which pivot screw 185 extends, one opening preferably being threaded and the other opening unthreaded similar to the openings 381, 383 in the first embodiment.

Figure 10B:
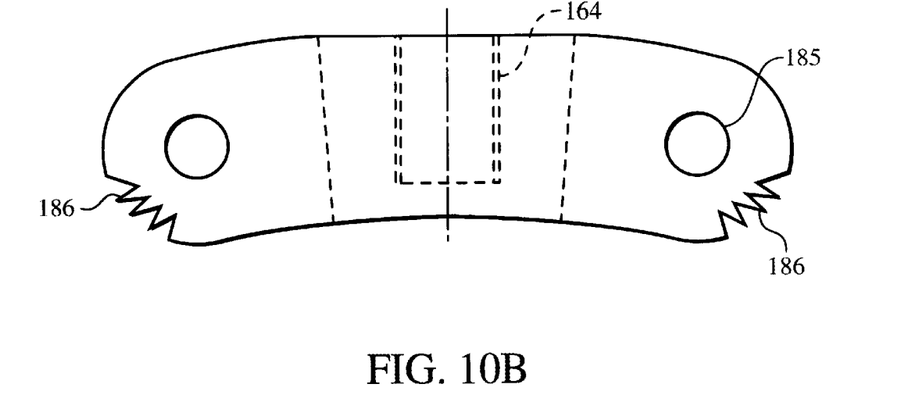

As shown in FIG. 10B, a portion of each mounting support 180, 182 is provided with ratchet teeth 186 for mating with a ratchet pawl 410 or 430 as previously described provided on arm member 400, 420. Ratchet pawl 410 or 430 interact with ratchet teeth 186 in the same way as previously described with respect to the first embodiment for rapid opening and closing of the curved arm members.

In the embodiment shown in FIG. 9, curved arm members 400, 420 form a planar ring. Preferably, the ring formed has a radius between four and five inches, for example, 4.25 inches. The ring formed preferably opens so that the ends of the arm members are separated by approximately 10 inches.

While a few embodiments of the present invention have been shown and described, it is to be understood that many changes and modifications may be made thereunto without departing from the spirit and scope of the invention as defined in the appended claims.

What is claimed is:

1. An adjustable ratchet retractor support apparatus for mounting on a threaded shaft comprising:

(a) a rotatable locking mount having first and second surfaces and an axis of rotation perpendicular to said surfaces;

(b) first and second rotatable pivot members disposed respectively on said first and second surfaces for rotation around said axis of rotation, each of said pivot members comprising ratchet teeth;

(c) first and second curved arm members mounted respectively on and associated respectively with said first and second pivot members, each of said arm members being rotatable about a respective axis of rotation perpendicular to the axis of rotation of said locking mount and having mounted thereon a ratchet pawl for engagement with said ratchet teeth of the associated pivot member; and (d) first and second rotatable clamps disposed respectively on said first and second pivot members for restraining rotation of said pivot members.

2. The adjustable ratchet support apparatus of claim 1 further comprising a ball post assembly having a threaded shaft disposed within said rotatable locking mount and said rotatable pivot members.

3. The adjustable ratchet support apparatus of claim 1 wherein each of said first and second arm members has a plurality of notches around an outside edge of said arm member.

4. The adjustable ratchet support apparatus of claim 1 wherein:

(a) each of said first and second surfaces of said locking mount have locking teeth;

(b) each of said first and second pivot members have locking teeth for interfacing with said locking teeth of said locking mount and restraining rotation of said pivot members.

5. The adjustable ratchet support apparatus of claim 1 wherein:

(a) each of said rotatable pivot members comprises a pair of mounting supports for mounting a respective one of said arm members to said pivot members, each of said arm member being mounted between said pair of mounting supports by a pivot screw, said ratchet teeth being disposed on said pair of mounting supports; and (b) each of said ratchet pawls comprises a pair of ratchet pawl members for engagement with said ratchet teeth.

6. The adjustable ratchet support apparatus of claim 1 wherein said first and second curved arm members have a closed position wherein said arm members touch each other to form a planar ring having a radius between four and five inches.

7. An adjustable ratchet retractor support apparatus for mounting on a threaded shaft which comprises:

(a) a connector comprising first and second sets of ratchet teeth;

(b) first and second curved arm members mounted to said connector, each of said arm members being rotatable around a respective axis of rotation perpendicular to said connector and having mounted thereon a respective ratchet pawl for engagement with a corresponding one of said sets of ratchet teeth.

8. The adjustable ratchet retractor support apparatus of claim 7 further comprising a ball post assembly having a threaded shaft disposed within said connector.

9. The adjustable ratchet support apparatus of claim 7 wherein each of said first and second arm members has a plurality of notches around an outside edge of said arm member.

10. The adjustable ratchet support apparatus of claim 7 wherein:
(a) said connector has first and second ends, each end comprising a pair of mounting supports for mounting a respective one of said arm members to said connector, each of said arm members being mounted between a corresponding one of said pair of mounting supports by a pivot screw, a corresponding one of said first and second sets of ratchet teeth being disposed on a respective one of said pair of mounting supports; and
(b) each of said ratchet pawls comprises a pair of ratchet pawl members for engagement with a respective one of said first and second sets of ratchet teeth.

\* \* \* \* \*

UNITED STATES PATENT AND TRADEMARK OFFICE
CERTIFICATE OF CORRECTION

PATENT NO. : 6,808,493 B1
DATED : October 26, 2004
INVENTOR(S) : Bookwalter et al.

It is certified that error appears in the above-identified patent and that said Letters Patent is hereby corrected as shown below:

<u>Title page,</u>
Item [73], Assignee, should read -- Flexbar Machine Corporation, Islandia, NY (US) --.

Signed and Sealed this

Twenty-eighth Day of December, 2004

JON W. DUDAS
*Director of the United States Patent and Trademark Office*